United States Patent [19]
Blyskal et al.

[11] Patent Number: 5,842,474
[45] Date of Patent: Dec. 1, 1998

[54] IUD LOADING DEVICE

[75] Inventors: Philip J. Blyskal, Princeton, N.J.;
Lance J. Bronnenkant, Snyder, N.Y.;
George A. Clark, Lewis Center, Ohio

[73] Assignee: FEI Products, Inc., North Tonawanda, N.Y.

[21] Appl. No.: 678,831

[22] Filed: Jul. 12, 1996

[51] Int. Cl.⁶ .................................................. A61F 6/14
[52] U.S. Cl. ........................................ 128/839; 128/840
[58] Field of Search ................................. 128/830–841

[56]  References Cited

U.S. PATENT DOCUMENTS

| | | |
|---|---|---|
| 3,515,132 | 6/1970 | McKnight ............................... 128/840 |
| 3,783,861 | 1/1974 | Abramson . |
| 3,918,444 | 11/1975 | Hoff ........................................ 128/840 |
| 3,965,891 | 6/1976 | Lerner . |
| 4,026,281 | 5/1977 | Mayberry et al. . |
| 4,143,656 | 3/1979 | Holmes . |
| 4,249,525 | 2/1981 | Krzminski . |
| 4,428,371 | 1/1984 | Krzminski . |
| 4,549,652 | 10/1985 | Free . |
| 4,562,835 | 1/1986 | Anderson . |
| 4,572,162 | 2/1986 | Livesay et al. . |
| 5,217,450 | 6/1993 | Pryor et al. . |
| 5,370,129 | 12/1994 | Diaz ........................................ 128/840 |

*Primary Examiner*—Michael A. Brown
*Attorney, Agent, or Firm*—Lerner, David, Littenberg, Krumholz & Mentlik

[57]  ABSTRACT

The present invention provides an IUD loading device which folds the extended portions of an IUD such that the IUD may be placed into an insertion tube.

22 Claims, 4 Drawing Sheets

IUD LOADING DEVICE

FIELD OF THE INVENTION

The invention relates to methods and apparatus that are useful for loading an IUD into an insertion tube as a prelude to placing an IUD into the uterus of a patient and kits useful for preparing an IUD for insertion.

BACKGROUND OF THE INVENTION

There are a wide variety of intrauterine contraceptive devices ("IUDs") available for use in birth control. These include generally "T" shaped devices such as those illustrated and described in U.S. Pat. Nos. 4,026,281, 4,562,835 and 4,572,162 as well as IUDs of other shapes. See also, for example, U.S. Pat. No. 4,428,371, U.S. Pat. No. 3,965,891 (FIGS. 12–20) and U.S. Pat. No. 3,783,861.

For the most part, it is desirable to fold the foldable portions of IUDs to facilitate the insertion thereof past the cervix of a patient. Folding can be accomplished in several ways depending upon a number of factors including the shape of the IUD. In fact, folding of an IUD can be accomplished manually or by the use of any number of devices such as those described in the aforementioned patents. Once an IUD is folded, it is placed into a hollow insertion tube which retains the extended portions of the IUD in a compacted or folded position. The entire assembly, i.e. the insertion tube containing the folded IUD can then be advanced into the uterus using various protocols. Once the IUD has cleared the cervix, it is ejected or releases out of the top of the insertion tube. This frees the folded or compacted portions of the IUD such that they are allowed to reextend to their normal, operable position.

From both a manufacturing standpoint and from the standpoint of the end user, it would be preferable to provide a ready-to-use kit including an IUD which already has been folded and packed into an insertion tube. Then, just before an insertion procedure, a doctor could remove the device which has been presterilized and maintained in a sterile package, insert the device through the cervix and eject it from the insertion tube into the uterus.

Unfortunately, due to the limitations of most IUDs, this is not possible. Due to the general memory of the materials used to make conventional IUDs, IUDs should not be compacted in an insertion tube for greater than about 5 minutes. If an IUD is retained in an insertion tube in a folded position for too long, creasing and permanent deformation can occur. This may severely limit the efficacy of the device and, in extreme circumstances, could raise potential health issues. Thus, a doctor or other health care professional must fold and pack the IUD into an insertion tube immediately prior to each procedure.

A number of protocols have been developed for allowing an IUD to be folded and packed into an insertion tube just prior to a surgical procedure. While many of these protocols can be effective, some protocols and devices still suffer from problems of undesirable deformation and creasing of the IUD. But perhaps the most common problem associated with many of these protocols is the difficulty in manipulating and folding the IUD and inserting it into the insertion tube, while maintaining the sterility and integrity of the system.

For example, U.S. Pat. No. 4,026,281 relates to methods and apparatus for inserting an IUD. The delivery device comprises a plunger adapted to receive the body of a substantially "T" shaped IUD. The delivery device also includes an insertion tube which is of sufficient diameter to allow for the plunger to be placed inside of same. The insertion tube is preferably flared at the bottom for easy insertion of the IUD. In operation and as shown in FIGS. 2 and 3 of the '281 patent, the IUD is first placed in the distal end of the plunger and then the plunger and IUD are forced into the bottom of the insertion tube. In the process, the extended arms of the "T" shaped IUD are compacted or folded by being forced to abut the flared bottom of the insertion tube. Once the IUD is placed in the proper position, it can be ejected out through the top of the insertion tube by advancing the plunger. The arms of the IUD, once released from the tube are allowed to return to an extended position.

Other known IUD folding and loading methods involve first folding the IUD and then inserting it into the top of an insertion tube. For example, U.S. Pat. No. 4,249,525 relates to an instrument for loading an IUD into an insertion tube. This device requires that a substantially "T" shaped IUD be placed into tracks within a folding device composed of rigid, converging walls. As the IUD is advanced, it abuts the walls and is forced to fold. Thereafter, the insertion tube can be slipped up over the body and over the ends of the folded arms to retain same. See also, U.S. Pat. No. 4,549,652.

In these later types of loading systems, the IUD must be advanced into some form of folding device which, at least temporarily, deforms the IUD such that it may be retained in an insertion tube. It is not difficult to imagine how such systems could be cumbersome. For example, and with reference again to the '525 patent, one must manipulate a "T" shaped IUD into the appropriate position, advance it with sufficient force to bend the arms of the IUD (but not its body), and maintain the IUD in the folded position for a time sufficient to allow the operator to insert the body and the folded ends of the IUD into an insertion tube. As if that were not cumbersome enough, consider the fact that IUDs of this type are commonly only 35 mm long and made of material which is only about 1–2 mm thick. Consider also that this must all be accomplished in a sterile IUD containing package, usually by a person wearing rubber gloves.

Manifestly, there remains a need for devices and methods of folding an IUD and placing it into an insertion tube which eliminates the awkward and cumbersome nature of the devices and protocols just discussed. Such devices and methods should provide ease of operation, simplicity of design and cost effectiveness in terms of manufacturing. The devices and protocols must not deform the IUD to an extent which would impair its operability. Moreover, folding must be quick and easy such that a doctor may fold and load the IUD and proceed with insertion before the integrity of the IUD is compromised.

SUMMARY OF THE INVENTION

The present invention addresses the aforementioned shortcomings of the prior art and provides the advantages of simplicity of design, operational ease and production cost effectiveness.

One aspect of the present invention provides an IUD loading device adapted for loading an IUD into an insertion tube. The IUD in question usually has at least one first arm or first foldable portion and a body portion which is not intended to be folded. The loading device includes: a stage or other surface on which is releasably positioned the IUD and a folding device which is movable relative to the stage as well as any IUD positioned in place thereon. The folding device has at least a first IUD engaging surface adapted to engage the first foldable portion of the IUD. The folding device is positively movable from a first position at which the first portion of the IUD is in an expandable position to a second position at which the first portion of the IUD is urged into a folded position. The movement of the folding device moves the first IUD engaging surface between a first position and a second position. Preferably, the movement of this first engaging surface is convergent. As the first engaging surface is in contact with the first arm of the IUD, this movement also causes the first arm of the IUD to fold from a first or extended position to a second or folded position. In a particularly preferred embodiment, the IUD is folded such that the arm(s) or foldable portions(s) and/or the body of the IUD are moved out of a single plane such that the ends of the arms actually rest over or under the body. For example, the extreme ends of a "T" shaped IUD can be manipulated to a position in which they are touching or almost touching on top of the body. In this way, the ends of the arms are brought into a position which is closer together than could be achieved by moving the ends along side of, and in the same plane as, the body of the IUD. Not only does this make it easier to place the IUD into an insertion tube, but it also helps maintain the generally cylindrical shape of the loaded tube. This helps minimize discomfort that the patient might otherwise experience when an insertion tube gets stretched into an elongated "oval" shape when loaded with IUD's in a conventional manner.

In certain preferred embodiments, the folding device also includes an insertion tube movably arranged with respect to the stage for temporarily retaining at least the first portion of the IUD after it has been urged into a folded position. It is also possible in accordance with this aspect of the present invention to use a folding device having a single movable IUD engaging surface to cause the folding of a plurality of foldable portions of an IUD. A plurality of folding devices each having a single IUD engaging surface is also contemplated.

In another aspect of the present invention, an IUD loading device is provided wherein a folding device, such as the one just described, also includes a second IUD engaging surface adapted to engage a second foldable portion of the IUD. The folding device is positively movable from a first position at which the first and second portions (if any) of the IUD are in expanded positions to a second position at which the first and second portions (if any) of the IUD are in folded positions. Both the first IUD engaging surface and the second IUD engaging surface can each move between respective first or divergent positions and second convergent positions by the movement of the folding device. The movement of the folding device causes the first arm of the IUD to fold from a first, extended position to a second, folded position and the second arm of the IUD to fold from a third extended position to a fourth, folded position.

Stated another way, the present invention is a device for folding and loading an IUD which includes a stage and a folding device. The stage includes at least one guide means which is adapted to direct the movement of an engaging surface of the folding device when the folding device is moved to fold the IUD. An IUD may be releasably positioned on the stage such that it may be folded.

This loading device has a number of advantages over prior devices. Principal among these advantages is that the IUD stays relatively stationary while the folding device moves and engages the foldable portions of the IUD and folds them into place. This virtually eliminates problems associated with directly contacting and manipulating the IUD. In fact, the device of the present invention all but eliminates the need for manual dexterity. By the use of the present invention, the foldable portions of an IUD are automatically folded into a proper position and retained in place. Thereafter, an insertion tube can be manipulated into place to retain the folded IUD. Indeed, because of the manner in which the ends of the arms cross out of the plane of the body of the IUD, loading into the insertion should be made particularly easy.

In addition, by use of the present invention, one need never worry about manipulating both the IUD and the insertion tube at the same time or urging the IUD against a compacting surface with too great an amount of force. This is a particular problem with devices such as those described in U.S. Pat. Nos. 4,249,525 and 4,549,652 wherein the IUD is folded and loaded into the top of an insertion tube. Of course, movement is relative and one can manipulate both the folded IUD and the insertion tube while loading.

Another advantage of the present invention is realized by the way in which the folding device engages the foldable portions of the IUD at a position which will not cause undue creasing or deformation. In accordance with the present invention, engaging surfaces can engage the peripheral ends of, for example, a "T" shaped IUD thereby distributing pressure over the entirety of each foldable arm. Instead of a typical bend, a "bowing" phenomena occurs which takes advantage of the full elasticity of the IUD without compromising its structural integrity.

In another particularly preferred aspect of the present invention there is provided an IUD insertion kit. The kit can include, inter alia, an IUD and a sterilizable tray including a stage and folding device as previously described. Preferably, the IUD is already positioned and retained on the stage before the kit is used. The folding device is positively movable relative to the stage and the IUD, and is disposed to fold the IUD upon moving. The folding device has a first IUD engaging surface adapted to engage the first foldable portion of the IUD and may also have a second IUD engaging surface adapted to engage a second foldable portion of the IUD. The folding device is movable from a first position to a second position such that the first IUD engaging surface and the second IUD engaging surface, if any, can each move between a first position and a second position. Preferably, they move between a divergent position and a convergent position. The movement of the folding device as described causes the first foldable portion of the IUD to fold from a first extended position to a second folded position and causes the second portion of the IUD, if any, to fold from a third extended position to a fourth folded position. The kit may also include an insertion tube disposed to be advanced over the folded IUD.

Most preferably, the kit would be totally enclosed, sterilized and ready to use. The IUD would already be in place on the stage and releasably retained thereupon. In operation, therefore, all one would have to do would be to engage the folding device to cause the folding or "bowing" of the foldable portions of the IUD followed by insertion of the folded IUD into a provided insertion tube. Thereafter, the entire assembly could be removed from the tray/package for direct insertion into a patient.

Methods for using the IUD insertion device in accordance with the present invention, as just described, are also contemplated hereby.

DETAILED DESCRIPTION OF THE PREFERRED EMBODIMENT

An IUD inserter in accordance with a preferred embodiment of the present invention is illustrated in FIGS. 1–8. For simplicity, the loading device 10 illustrated in these figures will be described in terms of the folding and loading of a substantially "T" shaped IUD having a first arm or first foldable portion 1, a second arm or second foldable portion 2 and a body or third portion 3. Of course, the loading device illustrated may also have applicability to the folding of IUDs having other shapes.

The loading device 10 includes a housing 12. Housing 12 may be formed as an integral part of a tray 300 (See FIG. 8) or, may be attached to a tray via slits (not shown) in the tray 300 using locking tabs 14. Housing 12 includes a stage 100 on which an IUD may rest, be positioned and be releasably retained. The size and shape of the stage will vary with the size and type of IUD and the arrangement and type of folding device 200. Stage 100 may include a recess 112 to accommodate the body 3 or third portion of the generally "T" shaped IUD and to assist in retaining same. Similar recesses may also be provided for various portions of IUD's of other shapes. Stage 100 may also include an insertion tube guide 110 which will assist the operator in maneuvering the folded IUD into the top aperture 4 of the insertion tube 5. This is accomplished by urging the insertion tube 4 into the proper position relative to the folded IUD.

Figure 1:
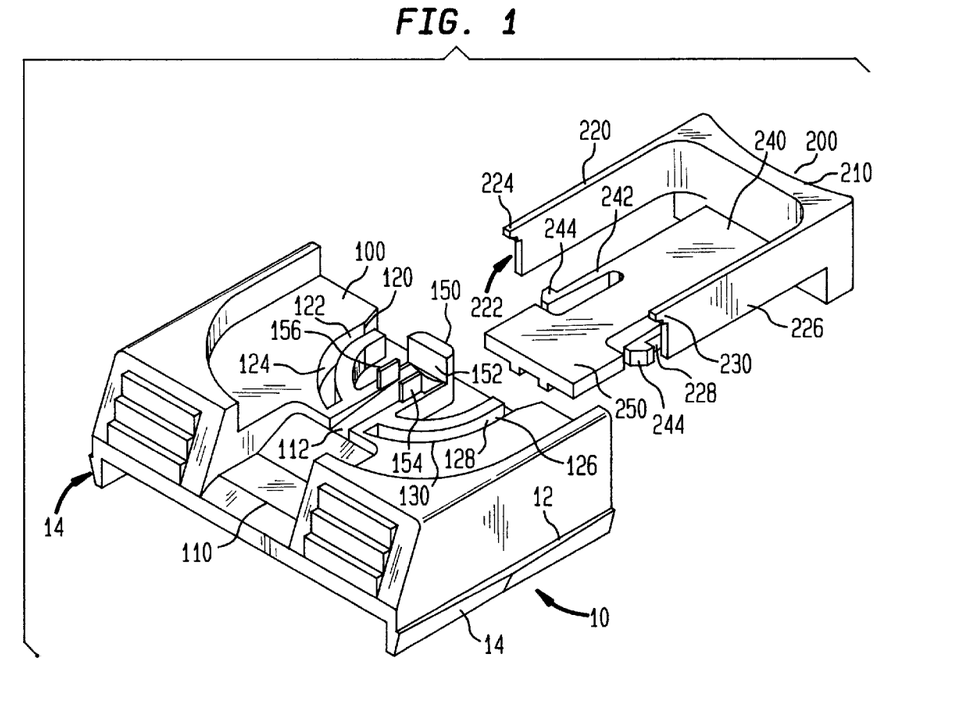
FIG. 1 is a front perspective view of a device in accordance with the present invention showing the folding device and stage in a disassembled configuration.

Stage 100 also includes at least one guide member 120 which, as illustrated in FIG. 1, is a groove. In this embodiment, groove 120 includes a first straight portion 122 and a second inwardly curving portion 124. Preferably, a second groove 126 including a second straight portion 128 and a second inwardly curving portion 130 is also provided herein. Grooves 120 and 126 receive arms 220 and 226 respectively of the folding device 200 as described herein. In this embodiment of the invention, the groove portions 122 and 128 are parallel relative to one another and groove portions 124 and 130 are convergent. Of course, the grooves could be divergent or even slightly convergent before portions 124 and 130 are reached. At that point, the degree of convergence increases. "Convergent" should be understood to mean that a groove, an engaging surface, an arm of a folding device and/or a foldable portion of an IUD is urged inwardly toward the body of an IUD positioned on the stage. It may also mean that the foldable portions of an IUD are moved into a position which is relatively closer to the body of the IUD. When more than one portion of an IUD is folded by the device of the present invention, "convergent" means that at least two foldable portions of the IUD are then brought into positions which are relatively closer to each other when in their expanded positions and relatively closer to the body as well. Preferably, at least two foldable portions are moved in opposite directions, i.e. clockwise and counterclockwise respectively.

Housing 12 also includes a retaining device 150. The retaining device 150 is intended to maintain the IUD in place and, in a proper position for folding and loading on stage 100. Any number of retaining devices 150 may be used. For example, stage 100 may include holes through which a piece of surgical thread can be run and looped around an IUD to retain it in place. The thread can be resilient but easily broken after the IUD has been loaded into the insertion tube. Similarly, a snap fitting may be used to retain the body 3 of the IUD such as those employed in, for example, thermometer cases and the like.

As shown in FIG. 1, however, the retaining device 150 may include a rear wall member 152 as well as perpendicularly disposed wall members 154 and 156. Each of these wall members are spaced apart from one another sufficiently to allow a portion of the IUD to fit therebetween. For example, body 3 of a substantially "T" shaped IUD can be placed between perpendicular members 154 and 156 which will prevent the IUD from moving horizontally or from being withdrawn through the front of the housing 12. Rear wall member 152 will prevent the rearward movement of the IUD, particularly when being placed inside an insertion tube.

Figure 5:
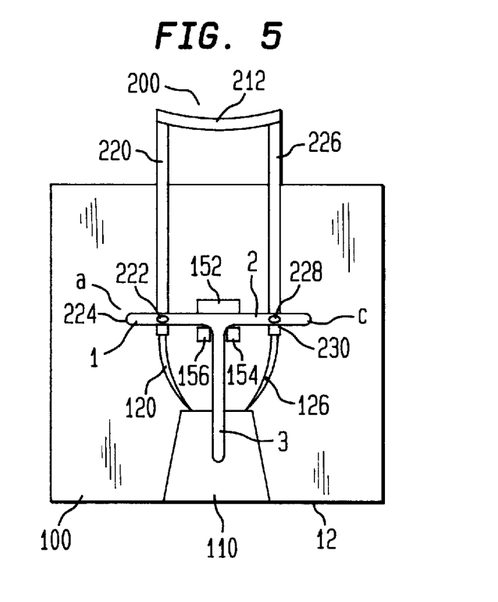
FIG. 5 is a top view of a preferred device in accordance with present invention showing engaging a "T" shaped IUD when the folding device is in the retracted position.
Figure 6:
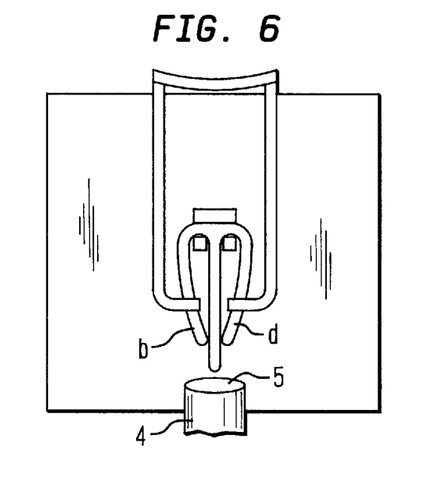
FIG. 6 is a top view of a preferred device in accordance with present invention showing engaging a "T" shaped IUD when the folding device is in the advanced position.

The loading device 10 also includes a folding device 200 which includes an actuation member 210. Actuation member 210 may be a button, lever, slide, handle or other device which can be manipulated. Attached to the sides of the actuation member 210 are arms 220 and 226 respectively. As shown in FIGS. 5 and 6, when folding device 200 is assembled with housing 12, a portion of arms 220 and 226 are retained within portions 122 and 128 of grooves 120 and 126 respectively. Arms 220 and 226 also include a first IUD engaging surface 222 and a second IUD engaging surface 228 respectively. Protrusions 224 and 230 act to positively retain the arms of the IUD in place both during folding and during storage or transport of the IUD prior to folding. Protrusions 224 and 230 also tend to urge the IUD against stage 100 as folding device 200 moves from its first to its second position.

When folding devise 200 is moved into the folding or convergent position the ends of arms 220 and 226 are forced in a generally convergent direction toward the body of an IUD seated on stage 100. However, while the lower portions of arms 220 and 226 are retained in grooves 120 and 126, the upper portions of the arms are not. These upper portions of the arms, as well as protrusions 224 and 230 will tend to diverge slightly relative to the lower portions of arms 220 and 226. The degree of divergence can be modified by adjusting the elasticity of the material use to produce the arms, by adjusting their physical dimensions and the like. This slight divergence is an advantage as it tends to reduce the hold that folding device 200 exerts on the folded IUD and allows the IUD to be more easily removed once placed in the end of an insertion tube. This arrangement also assists in the cross-over movement of the arms of the IUD relative to the body. To further reduce the hold that folding device 200 exerts on the folded IUD, one can also adjust the shape of the protrusions 224 and 230 such that their degree of engagement is reduced when they are in a generally convergent position.

Folding device 200 also includes an insertion member 240 which may include a pair of locking tabs 244 attached to the insertion member 240 via a pair of flexible arms 242. An insertion guide 250 is also provided at the leading end of insertion member 240.

Figure 2:
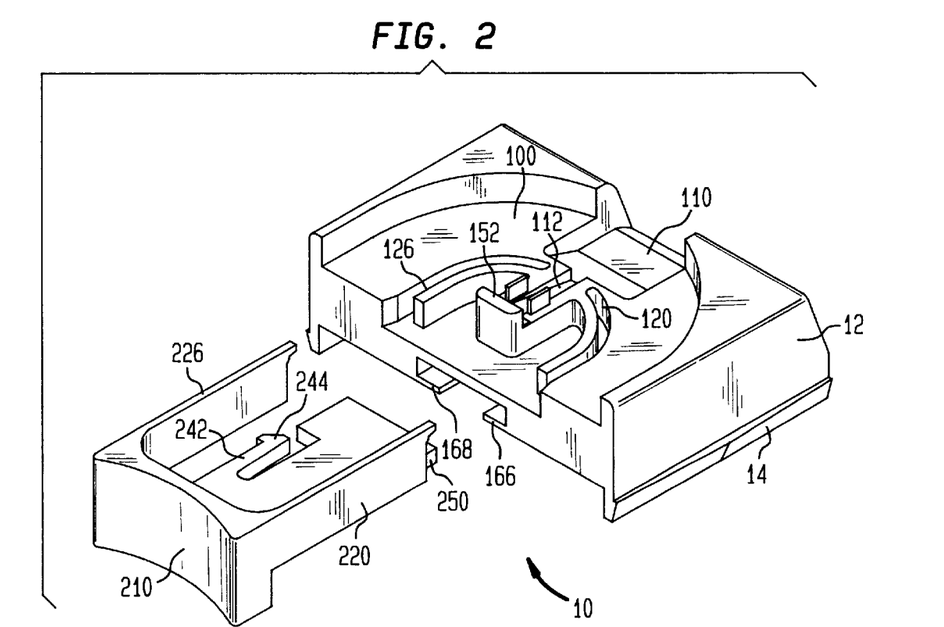
FIG. 2 is a rear perspective view of the device and elements illustrated in FIG. 1.
Figure 3:
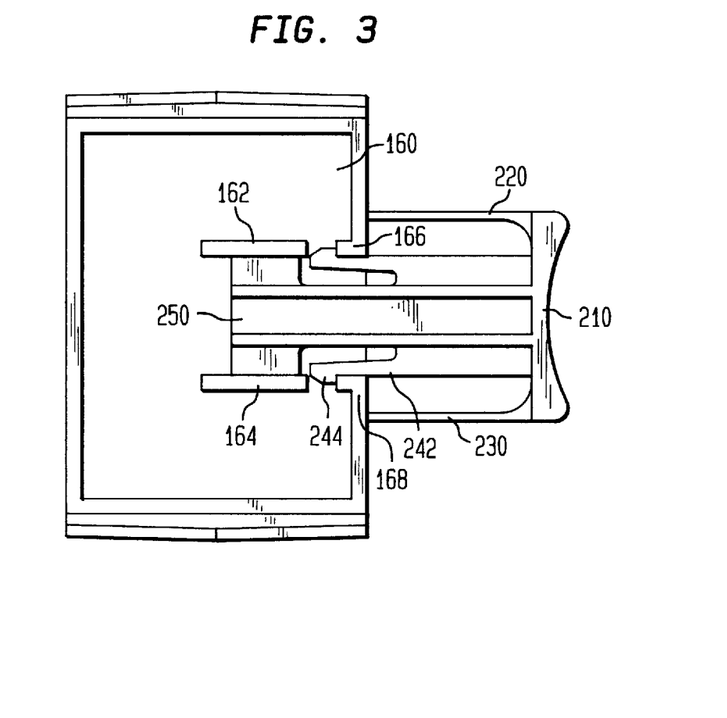
FIG. 3 is a bottom view of the device in accordance with the present invention with the folding device engaged within the housing.
Figure 4:
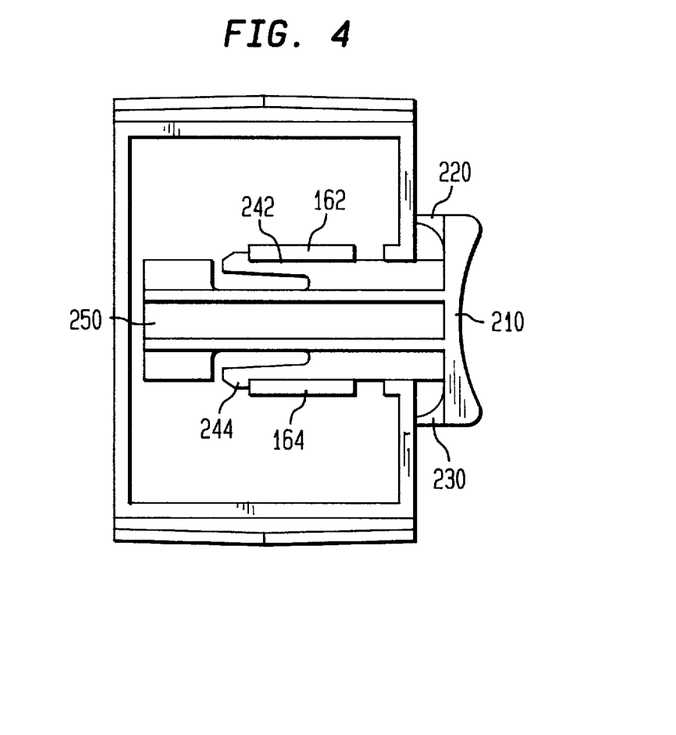
FIG. 4 is a bottom view of the device as illustrated in FIG. 3 showing the position of the folding device when in the advanced position.

As shown in FIG. 2, housing 12 also includes a first set of guide members 166 and 168 which are opposed to one another to form a gap into which insertion member 240 is inserted. As shown in FIGS. 3 and 4, housing 12 also includes a second set of guide members 162 and 164. Guide members 162 and 164 are spaced apart from one another by a distance which is sufficient to allow insertion member 240 to pass therebetween. The gap between guide members 166 and 168 is similarly sized. In addition there is a gap between guide members 162 and 166 and between 164 and 168 respectively. This gap is of a sufficient size to allow locking tabs 244 to rest therein in an expanded position.

When housing 12 and folding device 200 are joined cooperatively, as shown in FIGS. 3, 4, 5 and 6 arms 220 and 226 rest, at least in part, in grooves 120 and 126 respectively while insertion guide 250 is inserted through the aperture between guide members 166 and 168 until it rests between guide members 162 and 164. Folding device 200 is retained in place by locking tabs 244 which are disposed in the gaps between guide members 162 and 166 and 164 and 168 respectively, in an extended position. In that position, locking tabs 244 engage the inner surface of guide members 166 and 168 respectively. See FIG. 3.

When folding device 200 is moved from its first or retracted position, illustrated in FIGS. 3 and 5, to its second or advanced position, illustrated in FIGS. 4 and 6, locking tabs 244 are advanced forward where they abut and are forced inward by guide members 162 and 164. As folding device 200 continues to advance, locking tabs 244 are eventually pushed sufficiently such that they clear the opposed ends of guides 162 and 164. Then, locking tabs 244 are again allowed to return to an expanded position where they lock and engage guides 162 and 164. At the same time, arms 220 and 226 and the first and second engaging surfaces, 222 and 228 respectively, are advanced from a first position to a second position. In so doing, the arms 220 and 226 push the first portion 1 of the IUD from a first or extended position (a) to a second or folded position (b) and push the second portion 2 of the IUD from a third or extended position (c) to a fourth or folded position (d). Because of the expansion of locking tabs 244 and their engagement of guide members 162 and 164; the folding device 200 is retained in an advanced position with the IUD being retained in a folded arrangement.

Figure 10:
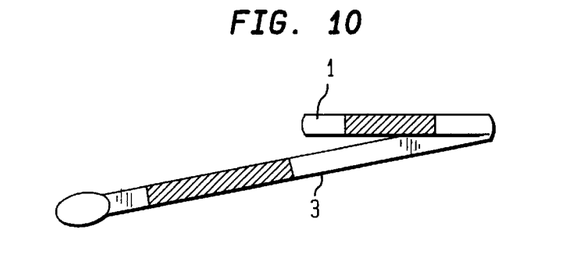
FIG. 10 is a side view of an IUD in a folded position when folded using a device in accordance with the present invention with the tip of the arm "crossing-over" the body thereof and with the body being moved downwardly out of its original plane.

The design and operation of a preferred embodiment of the loading device 10 just described actually urges the arm(s) or foldable portions(s) 1 and 2 and/or the body 3 of the IUD out of a single plane such that the ends of the arms actually rest over or under the body. For example, the extreme ends of a "T" shaped IUD can be manipulated to a position in which they are touching or almost touching on top of the body and/or each other. See FIG. 10. In this way, the ends of the arms are brought into a position which is closer together than could be achieved by moving the ends along side of, and in the same plane as, the body 3 of the IUD. Not only does this make it easier to place the IUD into an insertion tube, but it also helps maintain the generally cylindrical shape of the loaded tube. This helps minimize discomfort that the patient might otherwise experience when an insertion tube gets stretched into an elongated "oval" shape when loaded with IUD's in a conventional manner. Of course, it is not necessary to provide such a crossover motion in all instances.

By pulling folding device 200 back toward its first position, locking tabs 244 are compressed against the walls of guide members 162 and 164. Once they have cleared these guide members locking tabs 244 can reexpand in the gap between guide members 162 and 166 and 164 and 168 respectively, and engage guide members 162 and 164 to prevent the further removal of folding device 200 from housing 12. Of course, the loading device need not be designed to allow the folding device 200 to be returned to the first of generally divergent position. In fact in preferred embodiments, the loading device 10 is disposable and intended for a single use. In that case, the loading device 10 should be designed to make the locking of folding device 200 into the second of folding position irreversible. If a multiple use device is contemplated, however, than the insertion device 10 should also include some form of mechanism to allow folding device 200 to be released when desired.

As shown in FIG. 5, a substantially "T" shaped IUD having a first foldable portion 1, a second foldable portion 2 and a body third portion 3 can be positioned and retained on stage 100 by retention device 150. Retention device 150 is integrally molded with stage 100. The peripheral ends of portions 1 and 2 of the IUD abut and engage first IUD engaging surface 222 and second IUD engaging surface 228 respectively. At this point, portion 1 is located in an extended position (a) and portion 2 is located in an extended position (c), the folding device 200 is in a first, retracted position and arms 220 and 226 are in divergent positions. As illustrated in FIG. 6, when an operator manually engages folding device 200 by depressing activation member 210, folding device 200 is moved from its first position to the second or advanced position. Arms 220 and 226 are thereby forced forward with their movement being guided by grooves 120 and 126 respectively. As arms 220 and 226 are forced toward a second position, the first engaging surface 222 and second engaging surface 228, as well as IUD arms 1 and 2 are urged convergently toward body 3. This convergent motion is most pronounced once arms 220 and 226 enter the curved portions 124 and 130 of grooves 120 and 126 respectively. Folding device 200, when fully advanced, is retained in that position via the engagement of locking tabs 244 with guides 162 and 164 as previously explained. The first engaging surface 222 and second engaging surface 228 of arms 220 and 226 remain in intimate contact with arms 1 and 2 of the IUD respectively and indeed now retain same in a folded position. If folding device 200 were withdrawn back to the first position, then the resiliency of the material used to manufacture the IUD would allow portions 1 and 2 to return to substantially their original extended positions (a) and (c) respectively.

Generally, the first position of the folding device 200 illustrated in FIGS. 5 and 6 is a retracted position where the arms of the IUD are extended. But this need not be the case.

The device could be adapted such that folding device 200 would have to be withdrawn relative to the stage for the arms to engage and urge the IUD into a folded position. Similarly, the second position of the folding device need not be the advanced position illustrated in FIG. 6.

After portions 1 and 2 have been moved to the second (b) and fourth (d) positions respectively, an insertion tube 4 can be fitted over the adjacent ends of folded portions 1 and 2 and body 3 to retain same. This is accomplished by advancing tube 4 through guide 110 in housing 12. Then, the IUD, now wedged in insertion tube 4, can be removed from the retention device 150 and pulled free from the entire assembly for insertion. Again this movement is relative and the loading device including the folded IUD could be advanced toward a stationary insertion tube. In fact, both could be moved convergently at the same time.

Of course, other configurations are also possible. As previously described, any number of devices which can releasably restrain, retain and position an IUD on stage 100 are contemplated. Similarly, grooves 120 and 126 could be eliminated in favor of other guide means such as protruding walls, the inner surfaces of which would act as guides for arms 220 and/or 226. In addition, arms 220 and 226 could be replaced with semi-rigid structures such as, for example, wires or cables which could be guided from a divergent to a convergent position via a hollow tube.

Figure 9:
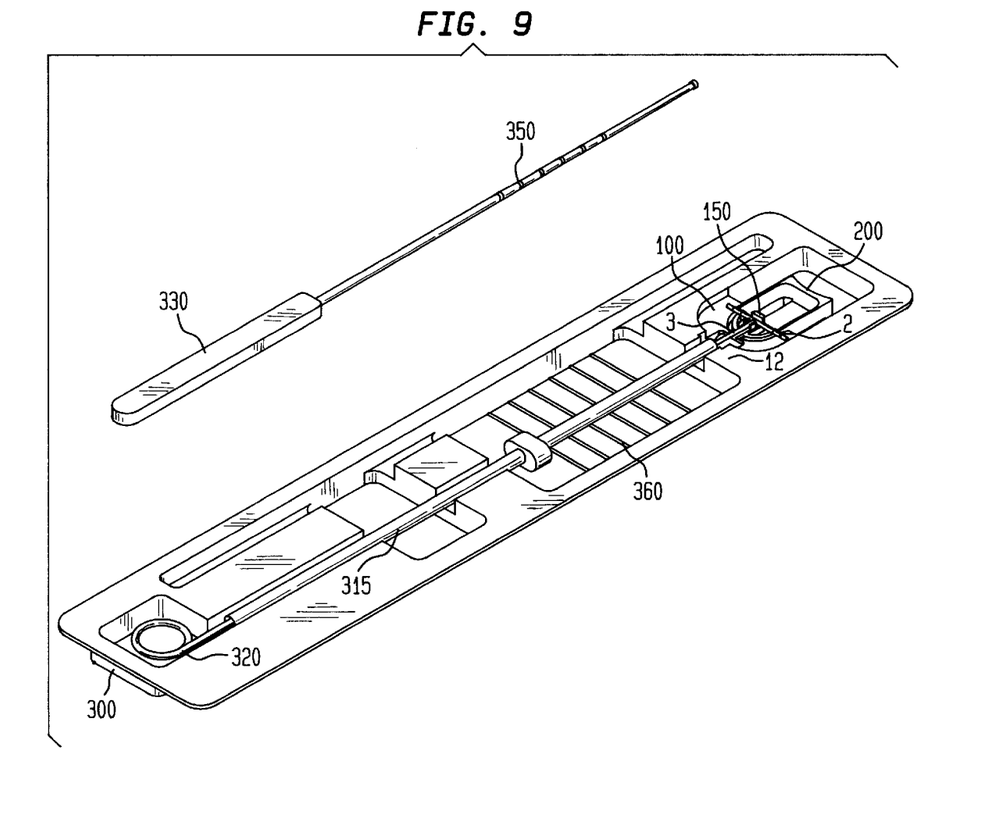
FIG. 9 is a top view of a kit in accordance with the present invention illustrating the IUD loading device of the present invention in a retracted position, an IUD retained in position on a stage which is part of a tray and an insertion tube and plunger also contained within the tray for loading the IUD into the insertion tube and inserting the IUD into the Uterus.

As shown in FIG. 9, housing 12 can be an integral part of a surgical preparation tray or prep tray 300. In fact, preferably, housing 12, including stage 100 and retention device 150, are all integrally molded with tray 300 in a single plastic piece. Folding device 200 can then be attached to housing 12 and, thereby, to the tray 300 as previously described. The kit would also include an IUD (1, 2, 3) as well as an insertion tube 310 and a device 320 for ejecting the IUD from the top of the insertion tube to deliver the IUD into the uterus. Typically, the tray would include an attached clear plastic cover (not shown) which would contain and retain the contents within the tray and maintain the sterility of all of the components. This cover can be at least partially peeled away to allow the IUD to be inserted into the insertion tube and to allow the insertion tube and IUD to be removed for a surgical procedure. The kit may also include, for example a uterine sound 330 which is used to measure the depth of the uterus and a depth gauge or flange 340 on the insertion tube. In a particularly preferred embodiment, the ridges (350) or other measuring indicia 350 on the uterine sound will correspond with ridges or indicia 360 on the tray making it easy for the medical profession to move the flange 340 to the correct depth.

Figure 7:
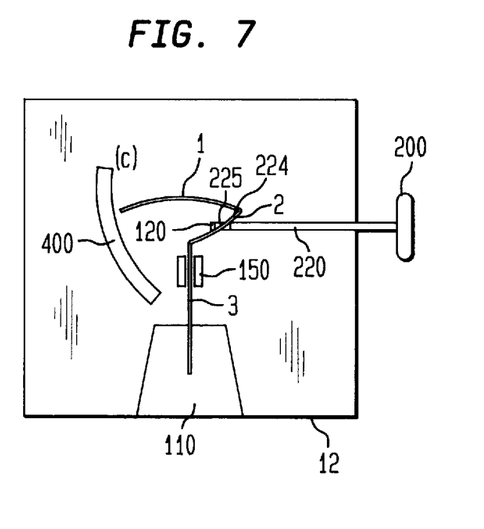
FIG. 7 is a top view of an alternate embodiment illustrating a sickle shaped IUD where the folding device has first and second movable IUD engaging surfaces.
Figure 8:
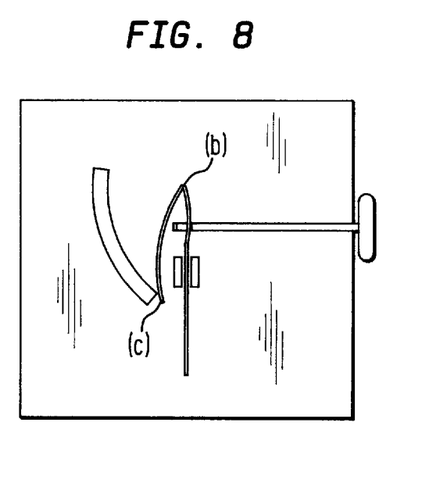
FIG. 8 is a top view of the device illustrated in FIG. 7 wherein the sickle shaped IUD is in a folded configuration.

While the invention has been described in terms of its use in conjunction with a substantially "T" shaped IUD, other forms of IUDs may also be utilized. For example, as shown in FIGS. 7 and 8 a sickle shaped IUD including a first curved section 1, a second curved section 2 attached at one end to an end of the first curved section 1 and at the other end to a third section 3 which forms the body of the IUD, may also be used. The IUD may be retained by a retaining device 150, such as, for example, a snap connector. The first section 1 of the sickle shaped IUD can be engaged by a first engaging surface 222 which travels through a generally curved groove 120 in housing 12 when folding device 200 is advanced from a retracted position to an advanced position. Simultaneously, the second section 2 of the sickle shaped IUD can be urged into a convergent position by moving folding device 201 from a retracted position to an advanced position thereby forcing arm 226 containing second engaging surface 228 to urge second section 2 of the IUD to a position which is more linear with respect to the body 3 of the IUD. Arm 226 will travel through a substantially linear groove 126 as illustrated.

The loading device and tray may be made from any material, however, disposable and recyclable plastics are preferred. The polymers used for the housing 12 must be capable of providing sufficient structural integrity to retain the IUD and the folding device and to force the arms of the folding device into their proper positions. The polymer used is also preferably low in cost, easily made using, for example, conventional injection molding techniques and is transparent. ABS resin and polycarbonates are examples of useful polymers. In contrast, the polymer used for the folding device must have sufficient flexibility to allow for the described operation of the arms 220 and 226. Acetal resins may be used to produce the folding device. All of the materials used should be able withstand sterilization by techniques such as ethylene oxide or gamma-radiation.

We claim:

1. An IUD loading device adapted for loading an IUD having at least one first portion attached to a body into an insertion tube said loading device comprising:
   a stage on which is releasably positioned the IUD;
      a folding device which is movable relative to said stage and the IUD, said folding device having at least a first IUD engaging surface adapted to engage the first portion of the IUD, said folding device being positively movable from a first position at which the first portion of the IUD is an expanded position to a second position at which the first portion of the IUD is urged into a folded position; and an insertion tube movably arranged with respect to said stage for temporarily retaining at least the first portion of the IUD after it has been urged to said folded position.

2. The IUD loading device of claim 1, further comprising at least one retention member disposed to cooperate with said stage to releasably retain the IUD on said stage.

3. The IUD loading device of claim 2, wherein at least a portion of said at least one retention member is integrally formed with said stage.

4. The IUD loading device of claim 1, wherein said first position of said folding device is a retracted position, said second position of said folding device is an advanced position and wherein said first IUD engaging surface is positively movable between a divergent position which is spaced apart from the body of an IUD positioned.

5. The IUD loading device of claim 1, further comprising a folding device including a second IUD engaging surface adapted to engage a second portion the IUD, said folding device being positively movable from said first position at which the first and the second portions of the IUD are in expanded positions to said second position such that at which the first and the second portions of the IUD are in a folded position.

6. The IUD loading device of claim 5, further comprising at least one retention member disposed to cooperate with said stage to releasably retain the IUD on said stage.

7. The IUD loading device of claim 6, wherein at least a portion of said retention device is integrally formed with said stage.

8. The IUD loading device of claim 5, wherein said first and said second IUD engaging surfaces are generally perpendicular to the body of a retained IUD when in a retracted position and generally parallel to the body of a retained IUD when in an advanced position.

9. The IUD loading device of claim 5, further comprising a device for releasably locking said folding device in place when said first and said second IUD engaging surfaces are in a convergent position.

10. The IUD loading device of claim 5, wherein said stage includes at least one guide member to urge said engaging surfaces of said folding device toward a convergent position when said folding devise is moved from said first position to said second position.

11. The IUD loading device of claim 10, wherein said at least one guide member is a groove disposed in said stage, said groove containing at least a portion of said folding device which travels through said groove once said folding device is moved from said first position to said second position.

12. The IUD loading device of claim 11, wherein said groove includes a first portion which runs substantially parallel to the body of an IUD and a second portion which converges inwardly toward the body of an IUD.

13. The IUD loading device of claim 5, wherein said stage and said folding device are associated with a tray for retaining an IUD and an insertion tube in a sterile environment.

14. The IUD loading device of claim 5, wherein said stage and said folding device are adapted to retain and fold a generally "T" shaped IUD.

15. An IUD loading device adapted for loading into an insertion tube an IUD having at least a first and a second portion attached to a body, said loading device comprising:

a stage on which is releasably positioned the IUD;

a folding device which is movable relative to said stage and the IUD, said folding device having a first IUD engaging surface adapted to engage the first portion of the IUD and having a second IUD engaging surface adapted to engage the second portion of the IUD, said folding device being positively movable from a first position at which said first IUD engaging surface and said second IUD engaging surface are in divergent positions and the first and the second portions of the IUD are in expanded positions, to a second position at which said first IUD engaging surface and said second IUD engaging surface are in convergent positions and the first and the second portions of the IUD are in folded positions.

16. An IUD loading device adapted for loading into an insertion tube an IUD including at least a first and a second foldable portion and a body, said device comprising: a positioning means for releasably retaining and positioning an IUD, a folding means which is positively movable with respect to said positioning means and said IUD for engaging a first and a second portion of the IUD and folding same and an insertion tube movably arranged with respect to said positioning means for temporarily retaining at least the first and second portions of the IUD after the portions have been folded.

17. An IUD loading device adapted for folding a generally "T" shaped IUD, said IUD including at least a first foldable portion having a first end, a second foldable portion having a second end and a body having a set thickness, said first end, said second end and said body defining a plane, said device comprising: a positioning means for releasably retaining and positioning an IUD, a folding means which is positively movable with respect to said positioning means and said IUD for engaging said first and said second portion of the IUD and folding same such that at least one of said first end, said second end and said body no longer occupy said plane.

18. The IUD loading device of claim 17 wherein when said IUD is folded, said first end of said first foldable portion and said second end of said second foldable portion are separated by gap which is less than the thickness of said body.

19. An IUD insertion kit comprising: an IUD having at least one first portion attached to a body, an IUD loading device adapted for loading into an insertion tube an IUD having at least one first portion attached to a body, said loading device including: a stage on which is releasably positioned the IUD;

a folding device which is movable relative to said stage and the IUD, said folding device having at least a first IUD engaging surface adapted to engage the first portion of the IUD, said folding device being positively movable from a first position at which the first portion of the IUD is an expanded position to a second position at which the first portion of the IUD is urged into a folded position; and an insertion tube movably arranged with respect to said stage for temporarily retaining at least the first portion of the IUD after it has been urged to said folded position.

20. The IUD insertion kit of claim 19, wherein said stage is integrally formed with said tray.

21. The IUD insertion kit of claim 20 further comprising a clear cover removably attached to said tray thereby providing a substantially sterile environment for folding said IUD and inserting at least a portion thereof into insertion tube.

22. A method of loading an IUD into an insertion tube comprising the steps of providing an IUD retained in a stationary position on a stage;

postively a folding device by moving the folding device relative to said IUD and said stage such that said folding device engages at least a portion of said IUD and urges the engaged portion of said IUD into a folded position;

and inserting at least said folded portion of said IUD into an insertion tube in such a manner that said IUD is retained in said folded position by said insertion tube once said folding device is retracted.

* * * * *

UNITED STATES PATENT AND TRADEMARK OFFICE
CERTIFICATE OF CORRECTION

PATENT NO. : 5,842,474

DATED : December 1, 1998

INVENTOR(S) : Blyskal et al.

It is certified that error appears in the above-identified patent and that said Letters Patent is hereby corrected as shown below:

Column 1, line 30, "releases" should be --released--.
Column 4, line 5, "insertion should" should read --insertion tube should--.
Column 5, line 25, "Uterus" should read --uterus--.
Column 6, line 49, "are" should read --is--.
Column 6, line 67, "use" should read --used--.
Column 8, line 11, "IUD's" should read --IUDs--
Column 8, line 28, "than" should read --then--.
Column 9, line 42, "example a" should read --example, a--.
Column 10, line 17, "able withstand" should read --able to withstand--.
Column 10, line 22, "tube said" should read --tube, said--.
Column 10, line 49, "portion the" should read --portion of the--.
Column 11, line 6, "devise" should read --device--.
Column 12, line 45, "postively" should read --positively--.

Signed and Sealed this

Twenty-seventh Day of April, 1999

*Attest:*

Q. TODD DICKINSON

*Attesting Officer*   *Acting Commissioner of Patents and Trademarks*